United States Patent
Pratap et al.

(10) Patent No.: US 7,365,218 B2
(45) Date of Patent: Apr. 29, 2008

(54) PROCESS FOR PREPARING GUGGULSTERONES

(75) Inventors: Ram Pratap, Lucknow (IN); Dharmendra Pratap Singh, Lucknow (IN); Raghavendra Pal, Lucknow (IN); Satyawan Singh, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 310 days.

(21) Appl. No.: 10/393,408

(22) Filed: Mar. 20, 2003

(65) Prior Publication Data

US 2004/0186306 A1 Sep. 23, 2004

(51) Int. Cl.
*C07J 7/10* (2006.01)
*C07J 13/00* (2006.01)
*C07J 1/00* (2006.01)

(52) U.S. Cl. ...................................... 552/638; 552/530

(58) Field of Classification Search ..................... None
See application file for complete search history.

(56) References Cited

OTHER PUBLICATIONS

Li et al. Studies on the epoxidation of 3b-hydroxy-5, 16-pregnadien-20-one acetate. Beijing Yixueyuan Xuebao (1983), 15(4), 328-9.*
Benn et al. The synthesis and stereochemistry of isomeric 16-hydroxy-17(20)-pregnenes. Journal of Organic Chemistry. (1964) vol. 29: pp. 1142-1148.*
Huang-Minlon. A simple modification of the Wolff-Kishner reduction. J Am Chem Soc. vol. 68, p. 2487-2488.*
Huang-Minlon. A simple modification of the Wolff-Kishner reduction. J Am Chem Soc. vol. 68, p. 2487-2488, (1946).*

* cited by examiner

*Primary Examiner*—Michael G. Hartley
*Assistant Examiner*—Jake M. Vu
(74) *Attorney, Agent, or Firm*—Ladas and Parry LLP

(57) ABSTRACT

The present invention provides an improved process for the preparation of Guggulsterones which comprises epoxidising 16-dihydropegnenolone acetate (16 DPA) by reacting 16DPA with hydrogen peroxide reagent adduct in the presence of a co-base in a polar solvent to obtain 3 β hydroxy-16 α, 17-oxido-5 pregnen-20-one, converting the 3 β hydroxy-16α, 17-oxido-5-pregnen-20-one by reacting with hydrazine in the presence of a strong base at refluxing temperature followed by oxidation to obtain desired guggulsterones viz. to 5, 17-(20)-cis and trans pregnadiene-3 β, 16-diol of the formula Ia and Ib.

10 Claims, No Drawings

PROCESS FOR PREPARING GUGGULSTERONES

FIELD OF THE INVENTION

The present invention relates to an improved process for preparing Guggulsterones. More particularly the present invention relates to a process for preparing a mixture of trans- and cis-4,17 (20) pregnadiene-3,16-dione (Guggulsterone-E and -Z respectively) of the formula Ia and Ib useful as hypolipidemic agent.

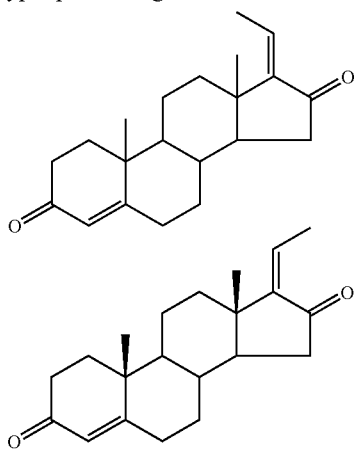

BACKGROUND OF THE INVENTION

The compound of the present invention is known in prior art literature as early as the nineteen seventies in connection with their utility in synthesis of steroidal alkaloids and saponines [S. V. Kessar and A. L. Rampal, Chem Ind., 1957 (1963); *Tetrahedron Letters,* 4319 (1966). These compounds were later isolated from the resin (gum guggul) obtained from *Commiphora mukul* which is an important drug in the Ayurvedic system for arthritis and inflammation.

There is also reference regarding its anti-obesity activity in Charak Sanghita [G. V. Satyavati in *Economic and Medicinal Plant Research*, Vol. 5, *Plants and Traditional Medicine* pp 47 (1991), Academic Press]. After extensive research work on gum-guggul through extractive fractionation followed by bio-evaluation at Central Drug Research Institute, Lucknow jointly with Malti-Chem Research Centre, Baroda, a toxicologically safe extract was standardized for hypolipidemic activity.

The product is being marketed as 'Guglip' by CIPLA Ltd., Bombay. It was simultaneously established in the study that hypolipidemic activity was due to presence of compounds of formula Ia and Ib above to the extent of 4-5% in the product and hence the name guggulsterone was coined to the product I.

The results of this pioneering work provoked considerable efforts among industries and academia world-over in Guglip and as a result several additional activities were established in the preparation such as prevention of sebum secretion [U.S. Pat. No. 5,6980, 948], anti-inflammatory by Bombardelli et al [U.S. Pat. No. 5,273,747] and use in benign prostate hypertrophy and acne. Bessett et al [U.S. Pat. No. 4,847,071 and 4, 847, 069] and Piazza et al [U.S. Pat. No. 5,521,223] disclosed photo-protective and anti wrinkle actions. Guggulsterone content in gugulipid is highest to the extent of 4-5% and therefore many of the activities of gugulipid have been implicated because of guggulsterone.

The hypolipidermic activity has already been established. In pursuance of further efforts in synthesis of guggulipid and its constituents, the process of guggulsterone synthesis has been further improved upon.

Two methods of guggulsterone synthesis are known. The first method is as follows:

5,17 (20)-pregnadiene-3,16-diol (Scheme I, compound V) is the key intermediate in the synthesis [WR Benn and RM Dodson, J. Org. Chem. 29, 1142 (1964)]. The reduction of α, β-unsaturated carbonyl function of 16-DPA with lithiumaluminumphydride (LAH) yields 5, 16-pregnadiene 3, 20-diol (III) which on catalyzed allylic rearrangement produces the key intermediate IV. The oxidation of IV yields guggulsterone.

However, the process has many drawbacks. During the process of reduction, a by-product through 1,4-hydride addition is always inevitable (to the extent of 40%) and hence a chromatographic separation is required. The slight impurity of this product will contaminate the final product with progesterone after oxidation on the other hand, use of pyrrophoric and inflammable reagents like LAH and solvent ether at industrial scale is also a cause of reluctance for industrial production [W. R. Benn, J. Org. Chem. 28, 3557 (196)].

The alternate process is as follows:

The unsaturated carbonyl function of 16-DPA is converted to 16,17-epozy carbonyl followed by Kishner reduction-elimination under Huang-Minlon condition yields the key intermediate (Scheme 2).

However, this procedure is also not suitable for large-scale preparation because of simultaneous formation of pyrazone, a by-product in appreciable high yields. The epoxidation with hydrogen peroxide is not reproducible instead a Michael addition product is obtained as a by-product in reported conditions. Also because of the supply of hydrogen peroxide of variable strength, it is difficult to fix the reaction parameters.

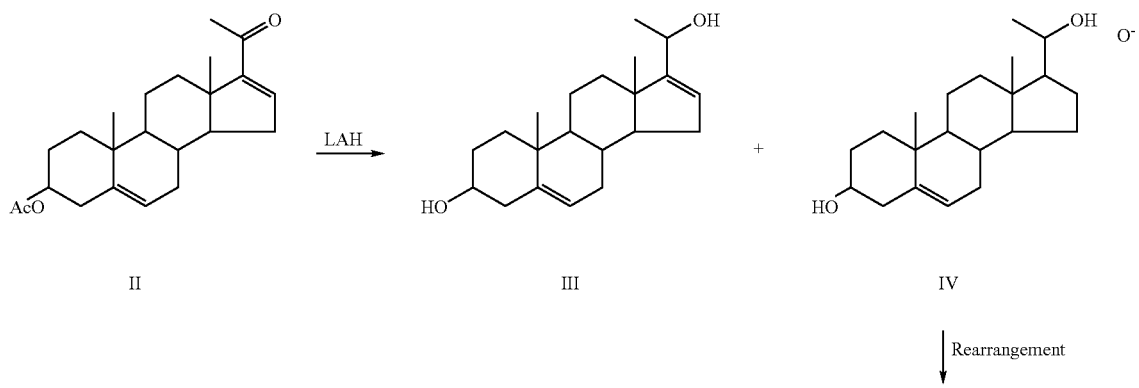

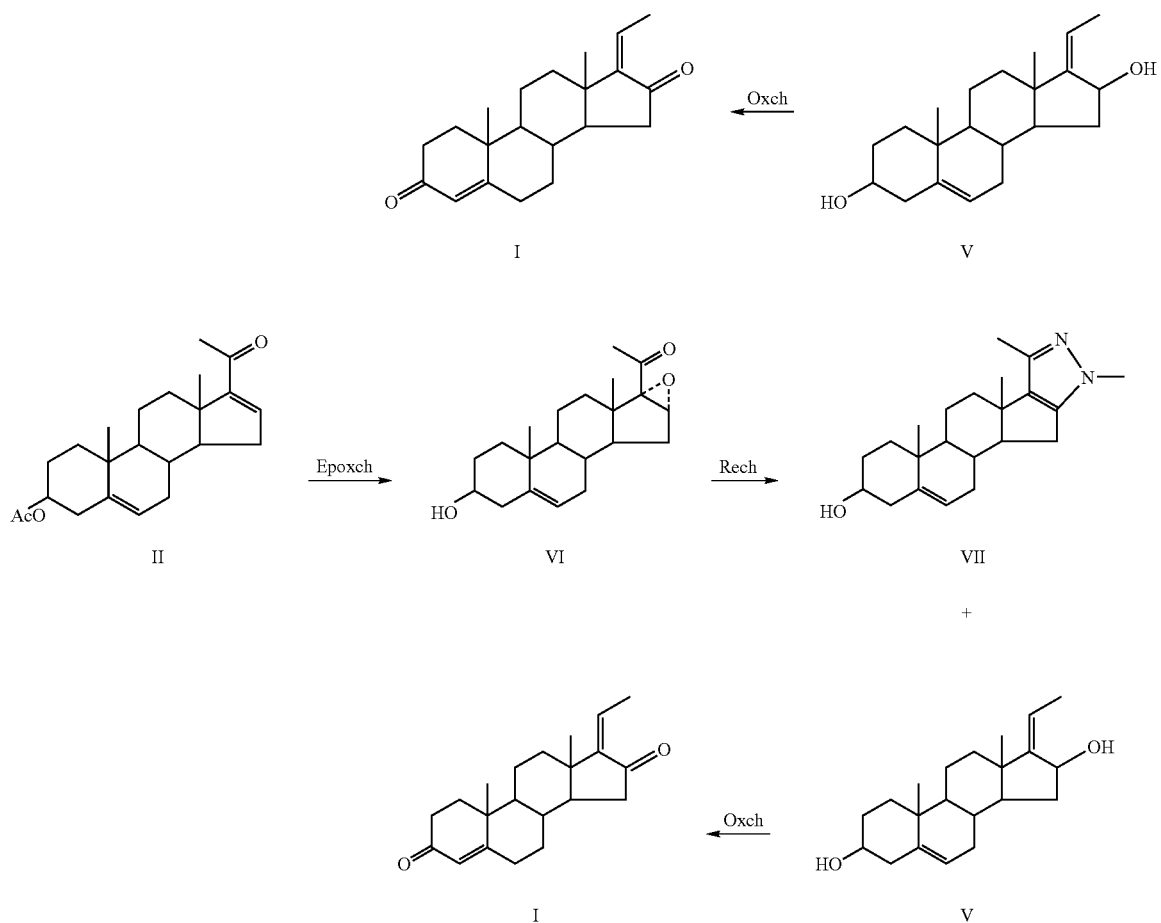

OBJECTS OF THE INVENTION

The main object of the invention is to provide an improved process for the preparation of Guggulsterones which obviates the drawbacks with the prior art enumerated above.

Another object of the invention is to provide a process using an oxidant, hydrogen peroxide on a solid support, which provide the reagent at the reaction site in high concentrations.

Yet another object of the invention is to provide a process in which no side product is produced.

SUMMARY OF THE INVENTION

Accordingly the present invention provides an improved process for the preparation of Guggulsterones which comprises epoxidising 16-dihydropegnenolone acetate (16 DPA) by reacting 16DPA with hydrogen peroxide reagent adduct in the presence of a co-base in a polar solvent to obtain 3 β hydroxy-16 α, 17-oxido-5 pregnen-20-one, converting the 3 βhydroxy-16α, 17-oxido-5-pregnen-20-one by reacting with hydrazine in the presence of a strong base at refluxing temperature followed by oxidation to obtain desired gugulsterones viz. to 5, 17-(20)-cis and trans pregnadiene-3 β, 16-diol of the formula Ia and Ib

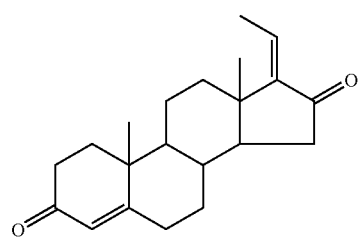

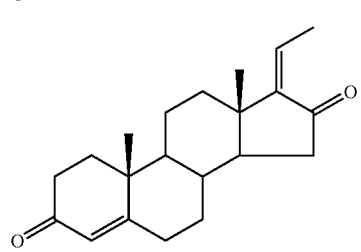

In one embodiment of the invention, the refluxing temperature is in the range of 100-1300° C.

In another embodiment of the invention the hydrogen peroxide-reagent adduct used is selected from hydrogen peroxide-urea adduct and hydrogen peroxide-sodium carbonate adduct.

In another embodiment of the invention the co-base is selected from the group consisting of sodium hydroxide, potassium hydroxide, lithium hydroxide and phase transfer catalyst.

In yet another embodiment of tie invention the polar solvent is selected from the group consisting of methanol, ethanol and a mixture thereof.

In a further embodiment of the invention the strong base is selected from the group consisting of trialkylamine, substituted amidine, guanidine potassium tertiarybutaoxide, alkalimetal-hexadimethylsilazane and lithiumdiisopropylamide.

DETAILED DESCRIPTION OF THE INVENTION

The present inventors therefore have made extensive research related to these problems. As a result, we analyzed the reactions very carefully to sort out the problems. The cause of sluggish epoxidation is the low percentage of oxidizing entity. We therefore used hydrogen peroxide on solid support in order to provide the reagent at the reaction site in high concentrations. The analysis of the mechanism of rearrangement reaction is depicted in Scheme III below, which suggest the intermediacy of hydrazone. There are two possible courses of reactions for hydrazone to undergo in subsequent step. In the first mode of reaction, the nucleophilic ring opening by nitrogen will provide pyrazone after aromatization. In the second mode, abstraction of a proton under the basis influence of hydrazine will generate N-anion, which may either stablize itself through resonance to another intermediate diazo or proceed for cyclization. However, it will not go for cyclization mode because in cyclization mode electron pair will rest on oxygen atom whereas in diazo intermediacy mode it will rest on carbon. Since carbon anion is more basis than oxygen anion and hence proton will prefer to stay at carbon anion. The cylization therefore should not prefer. The reaction from B to D is also not possible according to Baldwin's rule of cyclization. Hence, one the proton is abstracted fast, the by-product should not appear.

However, the abstraction of the first proton by hydrazine base (where N atomii has $sp^3$ hybridization) from the nitrogen atom of some hybridization ($sp^3$) is not a favourable proposition. As a result both possible modes of reaction operate to yield mixture of products The present invention therefore relates with the use of base of higher $pk_a$ value than hydrazine ($\Delta pk_a$) for rearrangement of epoxy hydrazone (generated in situ).

According to the present invention, a process for producing gugulsterone was improved to a large extent and with good efficiency as compared with the process disclosed by Benn, W. R. et al. in their publication [The synthesis and stereochemistry of isomeric 16-hydroxy-17 (20)-pregnenes, *J. Org. Chem.* 29: 1142-48 (1963)].

The compound obtained according to the process of the present invention is very useful as hypolipidemic and antoxidant agent and antioxidant agent. It can also be admixed with guglip and other hypolipidemic agents.

The following example is given by way of explanation and should not constructed the scope of the invention.

EXAMPLE

Step 1: Preparation of 16 α, 17-oxido-5-pregnen-20-one of the Formula (VI)

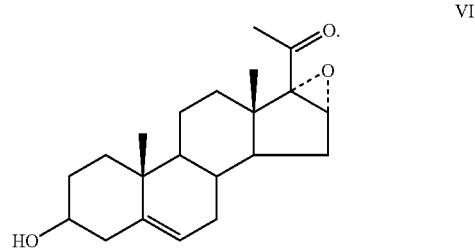

VI

16-Dehydropregnenolone acetate (35 g) is suspended in methanol (500 ml). The solution is treated, after cooling to

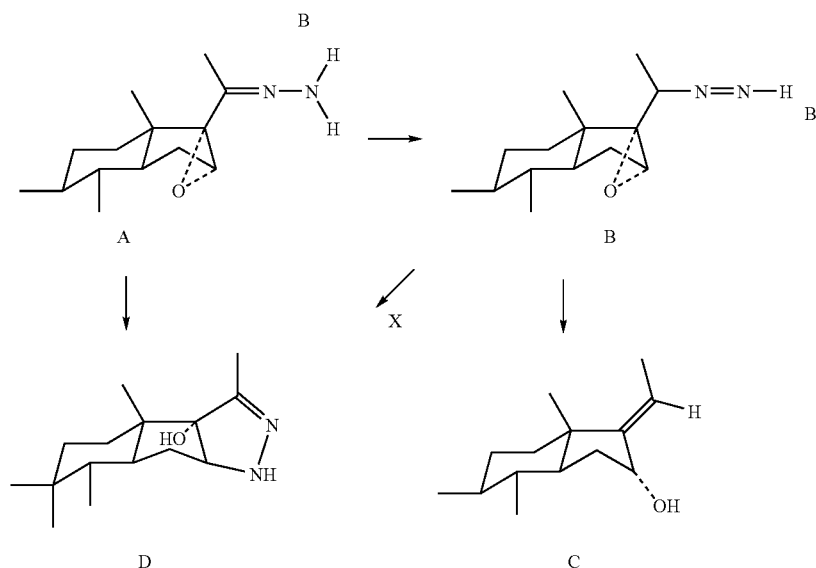

500° C. with 4N NaOH (8.9 gm in 50 ml H$_2$O) followed by immediately with hydrogen peroxide-urea adduct (UHP, 18 g.). The mixture is then stored in the refrigerator at 5° C. for 72 hr. The reaction mixture is shaken intermittently. The reaction mixture is poured into 500 ml of ice water. The product is isolated by centrifugation after wash up with water till neutrality to pH paper. The product is dried (63.0 g, 97%) M.P. 187-90 (187-90°).

$^1$H-NMR (CDCl$_3$): δ 5.3 (m, 1H, olefinic proton), 3.67 (s, $^1$H, C$_{16}$—H), 3.5 (m, $^1$H, C$_3$—H, 2.0 (s, 3H, CH$_3$CO); 1.2 and 1.0 (2s, 3H each, C$_{18}$Me, C$_{19}$Me).

Step 2: Preparation of 5, 17 (20)-cis and trans pregnadiene-3 β, -16-diol of the formula (V).

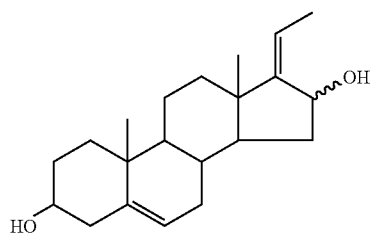

Va

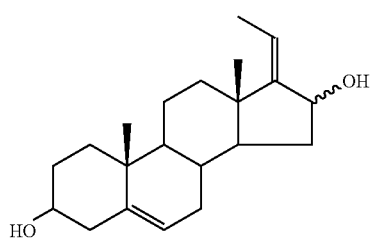

Vb

A suspension of 3 β-hydroxy-16 α, 17-oxido-5-pregnen-20-one (10 gm) in hydrazine (anhydrous, 100 ml), lithium-hexamethyldisilazane (10 ml, 1 Mol Sol) was brought slowly to reflux temperature (100-1200° C.) under stirring and protection of outlet with calcium chloride tube. The reaction was run till evolution of nitrogen (3-4 hrs) and then allowed to cooling to room temperature. The reaction mixture was poured in to ice water and product filtered and dried. Yield (9.0 g, 90%).

$^1$H-NMR (CDCl$_3$): δ 5.4 (m, $^1$H, olefinic H), 4.8 (m, $^1$H, olefinic H) 3.5 (m, $^1$H, C$_3$—H)

Step 3: Preparation of Guggulsterone of the Formula (Ia,b)

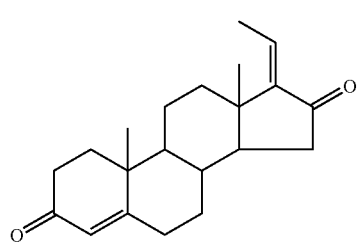

Ia

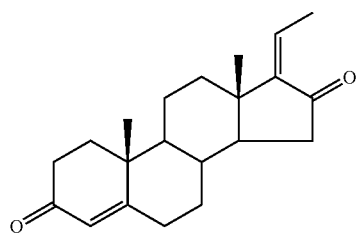

Ib

Diol V on oxidation with known reagents can be converted to the required product guggulstrone. The details are given below:

A three neck 2 lt. R.B. flask immersed in oil bath, is equipped with nitrogen inlet, mechanical stirrer and condenser with a device to remove some solvent during the course of reaction. The assembly is protected from moisture with calcium chloride guard tube. The flask is then charged with toluene (1200 ml) and started distillation of a portion of toluene in order to dry the system by azeotropic distillation. Then diol (30 g) and cyclohexanone (120 ml) are added to the flask. After an additional 50 ml of toluene has been distilled, aluminium isopropoxide (15 g) is added and toluene is kept on distilling dropwise till the reaction is complete so that about 600 ml of tolune has distilled. An additional 300 ml of tolune is distilled and then reaction is brought to room temperature. 400 ml of a saturated solution of Nak tartarate is added to the mixture and the organic layer becomes clear and orange. The nitrogen inlet is then removed and reaction was steam distilled to remove cyclohexanone. The reaction mixture is then cooled to room temperature and separated oil is extracted with ethyl acetate. Organic solution is then dried (Na$_2$SO$_4$) and solvent removed. The residual oil is chromatographed over flash silica gel column using hexane, toluene and ethyl acetate. The yield is 61% white amorphous powder having melting point 150-540° C.

What is claimed is:

1. A process for preparing Guggulsterones which comprises epoxidising 16-dihydropegnenolone acetate (16 DPA) by reacting 16DPA with a hydrogen peroxide reagent adduct on a solid support selected from hydrogen peroxide-urea adduct and hydrogen peroxide-sodium carbonate adduct in the presence of a co-base in a polar solvent to obtain 3 β hydroxy-16 α, 17-oxido-5 pregnen-20-one, reacting the isolated 3 β hydroxy-16α, 17-oxido-5pregnen-20-one with an anhydrous hydrazine in the presence of a base selected from the group consisting of trialkylamine, guanidine potassium tertiarybutaoxide, alkalimetal-hexadimethylsilazane, and lithium diisopropylamide or a mixture thereof at reflux temperature followed by oxidation to obtain-5, 17-(20)-cis and trans pregnadiene-3 β, 16-diol of the formula Va and Vb

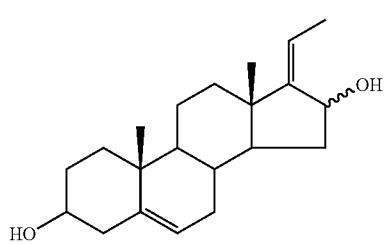

Va

-continued

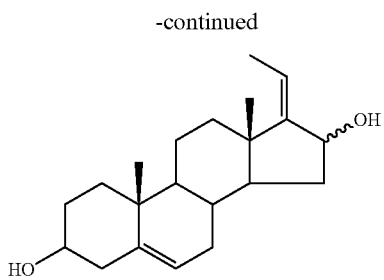
Vb said 5, 17-(20)-cis and trans pregnadiene-3 β, 16 diol are obtained without chromatographic separation, and oxidizing the 5,17-(20)-cis and trans pregnadiene 3 β,16 diol to obtain guggulsterones of formula Ia and Ib

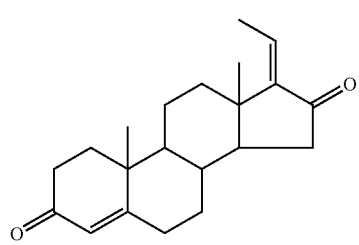
Ia

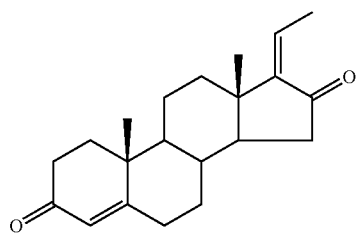
Ib

2. A process as claimed in claim 1 wherein the reflux temperature is in the range of 100-1300° C.

3. A process as claimed in claim 1 wherein the co-base is selected from the group consisting of sodium hydroxide, potassium hydroxide, and lithium hydroxide or a mixture thereof.

4. A process as claimed in claim 1 wherein the polar solvent is selected from the group consisting of methanol and ethanol or a mixture thereof.

5. A process for preparing Guggulsterones which comprises epoxidising 16-dihydropegnenolone acetate (16 DPA) by reacting 16DPA with a hydrogen peroxide reagent adduct on a solid support selected from hydrogen peroxide-urea adduct and hydrogen peroxide-sodium carbonate adduct in the presence of a co-base in a polar solvent to obtain 3 β hydroxy-16 α, 17-oxido-5 pregnen-20-one, converting the isolated the 3 βhydroxy-16α, 17-oxido-5-pregnen-20-one by reacting with a anhydrous hydrazine in the presence of a substituted amidine at reflux temperature followed by oxidation to obtain-5, 17-(20)-cis and trans pregnadiene-3 β, 16-diol of the formula Va and Vb

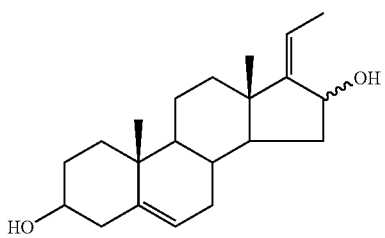
Va

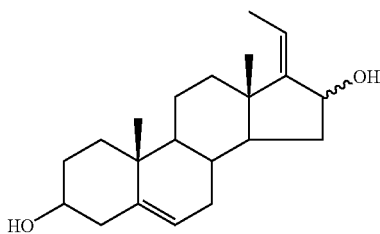
Vb said 5, 17-(20)-cis and trans pregnadiene-3 β, 16 diol are obtained without chromatographic separation, and oxidizing the 5,17-(20)-cis and trans pregnadiene 3 β, 16 diol to obtain guggulsterones of formula Ia and Ib

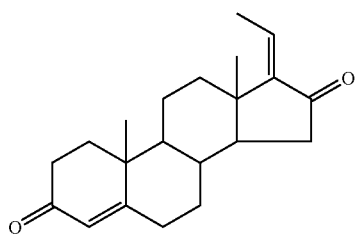
Ia

Ib

6. The process as claimed in claim 5 wherein the co-base is selected from the group consisting of sodium hydroxide, potassium hydroxide, and lithium hydroxide or a mixture thereof.

7. The process as claimed in claim 5 wherein the polar solvent is selected from the group consisting of methanol and ethanol or a mixture thereof.

8. A process for preparing Guggulsterones which comprises epoxidising 16-dihydropegnenolone acetate (16 DPA) by reacting 16DPA with hydrogen peroxide reagent adduct on a solid support selected from hydrogen peroxide-urea adduct and hydrogen peroxide-sodium carbonate adduct in the presence of a co-base selected from the group consisting of sodium hydroxide, potassium hydroxide, and lithium hydroxide or a mixture thereof in a polar solvent to obtain 3 β hydroxy-16 α, 17-oxido-5 pregnen-20-one, converting the isolated the 3 β hydroxy-16α, 17-oxido-5-pregnen-20-one by reacting with an anhydrous hydrazine in the presence of a base selected from trialkylamine, guanidine potassium tertiarybutaoxide alkalimetal-hexadimethylsilazane, and lithium diisopropylamide or a mixture thereof at reflux temperature followed by oxidation to obtain-5, 17-(20)-cis and trans pregnadiene-3 β, 16-diol of the formula Va and Vb

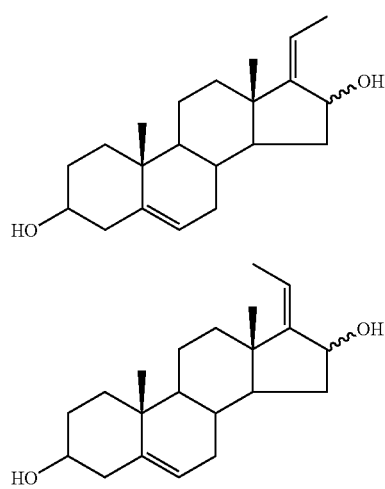

Va

Vb said 5, 17-(20)-cis and trans pregnadiene-3 β, 16 diol are obtained without chromatographic separation, and oxidizing the 5,17-(20)-cis and trans pregnadiene 3 β,16 diol to obtain guggulsterones of formula Ia and Ib

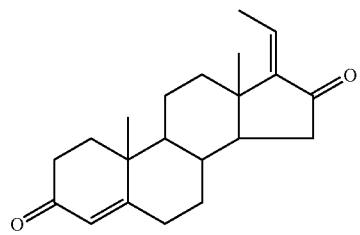

Ia

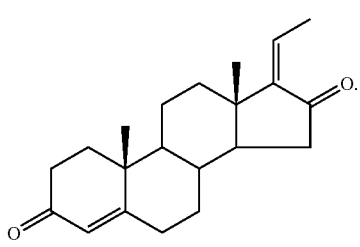

Ib

9. The process as claimed in claim 1 wherein the alkalimetal-hexadimethyl silazane is lithium hexadimethyl silazane.

10. The process as claimed in claim 8 wherein the alkalimetal-hexadimethyl silazane is lithium hexadimethyl silazane.

* * * * *